United States Patent
Hsiao et al.

(10) Patent No.: US 7,426,856 B2
(45) Date of Patent: Sep. 23, 2008

(54) DEVICE AND METHOD FOR MEASURING ADHESION STRENGTH BETWEEN TWO OPTICAL ELEMENTS

(75) Inventors: Bor-Yuan Hsiao, Taipei Hsien (TW); Mong-Tung Lin, Taipei Hsien (TW)

(73) Assignee: Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 51 days.

(21) Appl. No.: 11/617,142

(22) Filed: Dec. 28, 2006

(65) Prior Publication Data

US 2008/0053238 A1  Mar. 6, 2008

(30) Foreign Application Priority Data

Sep. 1, 2006  (CN) .................. 2006 1 0062445

(51) Int. Cl.
*G01N 19/04* (2006.01)
(52) U.S. Cl. ................... 73/150 A; 73/800; 73/827
(58) Field of Classification Search .......... 73/150 A, 73/800, 827
See application file for complete search history.

(56) References Cited

U.S. PATENT DOCUMENTS

| 2,894,388 | A | * | 7/1959 | Cook et al. ............... 73/54.22 |
| 4,194,392 | A | * | 3/1980 | Lombard et al. .......... 73/150 A |
| 4,934,185 | A | * | 6/1990 | Nishiyama et al. ........ 73/150 A |
| 6,813,958 | B2 | * | 11/2004 | Crosby et al. .............. 506/12 |
| 6,972,141 | B1 | * | 12/2005 | Bries et al. ................ 428/40.1 |
| 7,112,954 | B2 | * | 9/2006 | Palazoglu et al. .......... 324/204 |
| 2004/0228387 | A1 | * | 11/2004 | Palazoglu et al. .......... 374/163 |
| 2006/0171579 | A1 | * | 8/2006 | Lee et al. .................. 382/141 |
| 2007/0018639 | A1 | * | 1/2007 | Palazoglu et al. .......... 324/204 |

* cited by examiner

*Primary Examiner*—Edward Lefkowitz
*Assistant Examiner*—Freddie Kirkland, III

(57) ABSTRACT

A device for measuring adhesion strength between a first optical element and a second optical element includes a force gauge, a first magnet, and a second magnet. The second magnet is fixed to the force gauge. The first magnet and the second magnet are configured for magnetically attaching to opposite sides of the first optical element. An attractive force between the first magnet and the second magnet is greater than the adhesion strength between the first optical element and the second optical element.

15 Claims, 7 Drawing Sheets

DEVICE AND METHOD FOR MEASURING ADHESION STRENGTH BETWEEN TWO OPTICAL ELEMENTS

BACKGROUND

1. Technical Field

The present invention relates to devices and methods for measuring adhesion strength between two optical elements.

2. Description of Related Art

Generally, image pick-up devices such as charge coupled devices (CCD) or complementary metal oxide semiconductors (CMOS) used in, for example, cameras, react to light even in the near-infrared region beginning at a wavelength of about 700 nanometers and in the infrared (IR) region. However, light in the near-infrared and IR regions causes crosstalk that reduces a signal-to-noise ratio of the image pick-up device and thereby deteriorating the device's reproduction ability. In order to prevent such reaction and crosstalk, IR cut filters that block light in the near-infrared and IR regions are assembled in lens modules implemented in conventional cameras.

In a conventional lens module, the IR-cut filter is usually attached to a spacer using glue. However, the usage of glue has adhesion and reliability problems. The IR-cut filter may become separated from the lens module due to weak adhesion strength. Therefore, it is necessary to measure the adhesion strength between the IR-cut filter and the spacer in lens module manufacturing.

It is therefore desirable to find a device and a method which can overcome the above mentioned problems.

SUMMARY

A method for measuring adhesion strength between a first optical element and a second optical element is provided. The first optical element has a first surface and an opposite second surface. The second optical element is adhered to the first surface of first optical element, and defines an opening therein. Accordingly a portion of the first surface of the first optical element is exposed to an exterior. The method comprises the steps of:

placing a first magnet on the exposed portion of the first surface of the first optical element and a second magnet on the second surface of the first optical element in such a manner that the first magnet and the second magnet are magnetically attached onto the first and second surfaces of the first optical element, wherein a magnetic force between the first magnet and the second magnet is greater than the adhesion strength between the first optical element and the second optical element;

attaching the second magnet to a force gauge;

attaching the second optical element to a fixture;

exerting an increasing force onto the force gauge in a direction away from the second optical element until the first optical element is pulled off the second optical element; and obtaining a measurement result from the force gauge, and then calculating the adhesion strength between the first and second optical elements based on the measurement result of the force gauge; and displaying the adhesion strength to a user.

A device for measuring adhesion strength between a first optical element and a second optical element includes a force gauge, a first magnet, and a second magnet. The second magnet is fixed to the force gauge. The first magnet and the second magnet are configured for magnetically attaching to opposite sides of the first optical element. An attractive force between the first magnet and the second magnet is greater than the adhesion strength between the first optical element and the second optical element.

BRIEF DESCRIPTION OF THE DRAWINGS

Many aspects of embodiments can be better understood with reference to the following drawings. The components in the drawings are not necessarily drawn to scale, the emphasis instead being placed upon clearly illustrating the principles of the present embodiment. Moreover, in the drawings, like reference numerals designate corresponding parts throughout the several views.

FIGS. 1 to 6 are schematic, cross-sectional views illustrating successive stages of a method for measuring an adhesion strength between an optical element and a spacer in a lens module, wherein FIG. 1 is a schematic, cross-sectional view of a lens module with a barrel, a spacer, and an IR-cut filter;

FIG. 2 is a schematic, cross-sectional view of the lens module together with a base and a first magnet;

FIG. 3 is a schematic, cross-sectional view of the lens module together with the base and the first magnet, wherein the barrel is attached to the base;

FIG. 4 is a schematic, cross-sectional view of the lens module together with the base, the first magnet, and a second magnet, wherein the first magnet attracts the second magnet together;

FIG. 5 is a schematic, cross-sectional view of the lens module together with the base, the first magnet, the second magnet, and a force gauge, wherein the force gauge is fixed to the second magnet; and FIG. 6 is a schematic, cross-sectional view of the lens module together with the base, the first magnet, the second magnet, and the force gauge, wherein the IR-cut filter is pulled off from the spacer using the force gauge.

DETAILED DESCRIPTION OF THE EMBODIMENTS

Embodiments will now be described in detail below with reference to the drawings.

Figure 1:
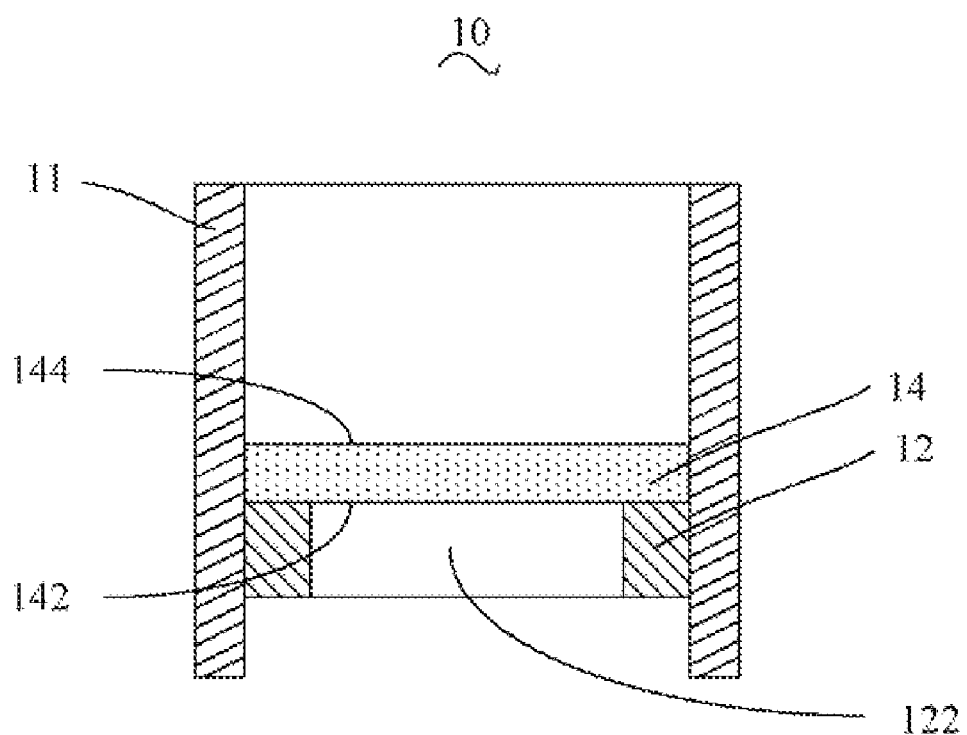
Figure 2:
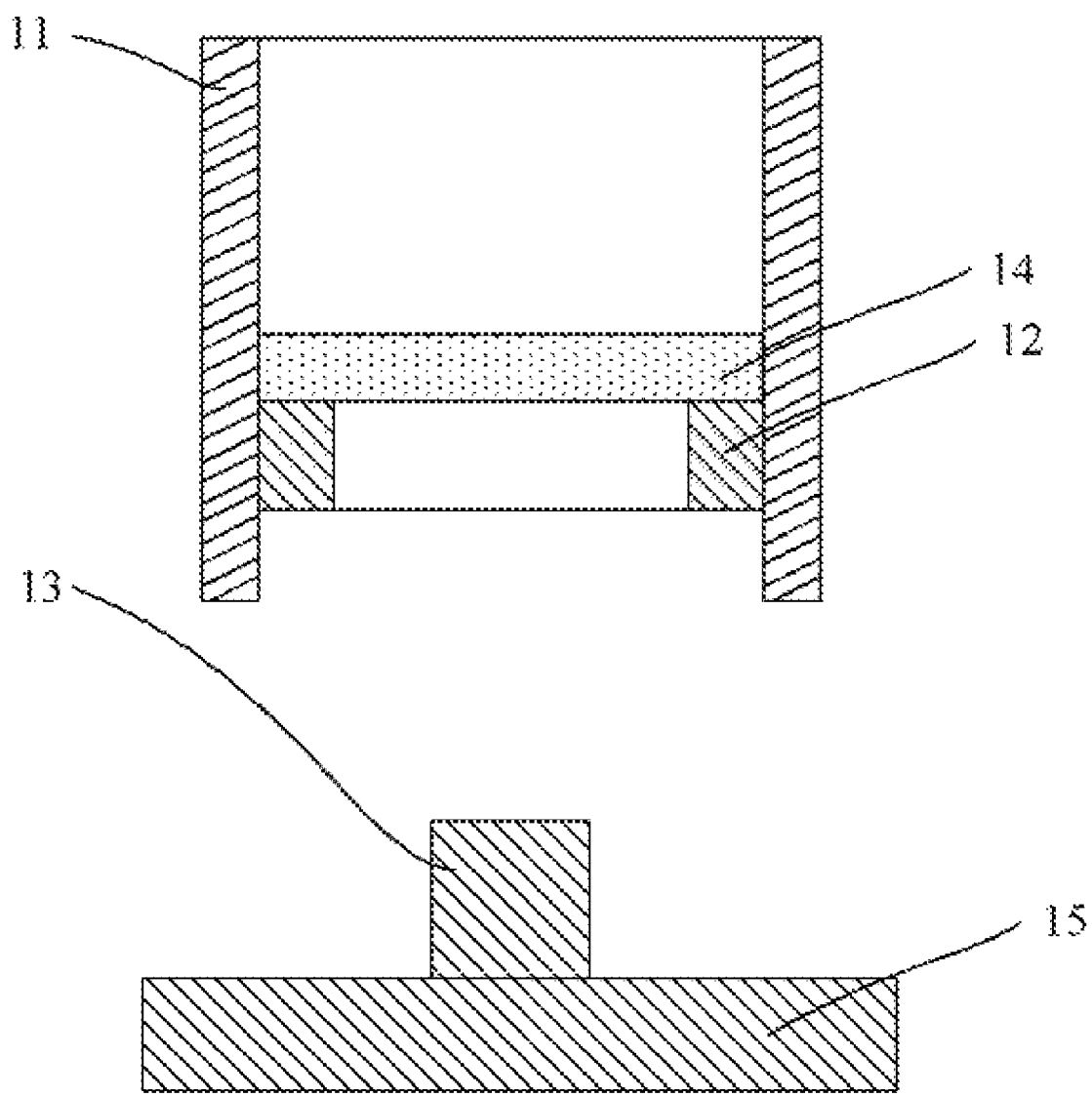

A method for measuring adhesion strength between a first optical element and a second optical element is provided. The first optical element can be an IR-cut filter, a lens, and so on. The second optical element can be, for example, a spacer. As an example, a method for measuring adhesion strength between the IR-cut filter and the spacer will be described as follows:

Referring to FIG. 1, a lens module 10 is provided. The lens module 10 includes a barrel 11, a spacer 12, and an IR-cut filter 14 received in the barrel 11. The spacer 12 defines a circular opening 122 therein and is fixed in the barrel 11. The IR-cut filter 14 includes a first surface 142 and an opposite second surface 144, and is fixed on the spacer 12 using glue. Accordingly, a portion of a first surface 142 is exposed to an exterior. The adhesion strength between the IR-cut filter and the spacer 12 will be measured in following steps:

Referring to FIG. 2, a base 15 and a first magnet 13 are provided. The first magnet 13 is placed on the base 15, but not attached to the base 15.

Figure 3:
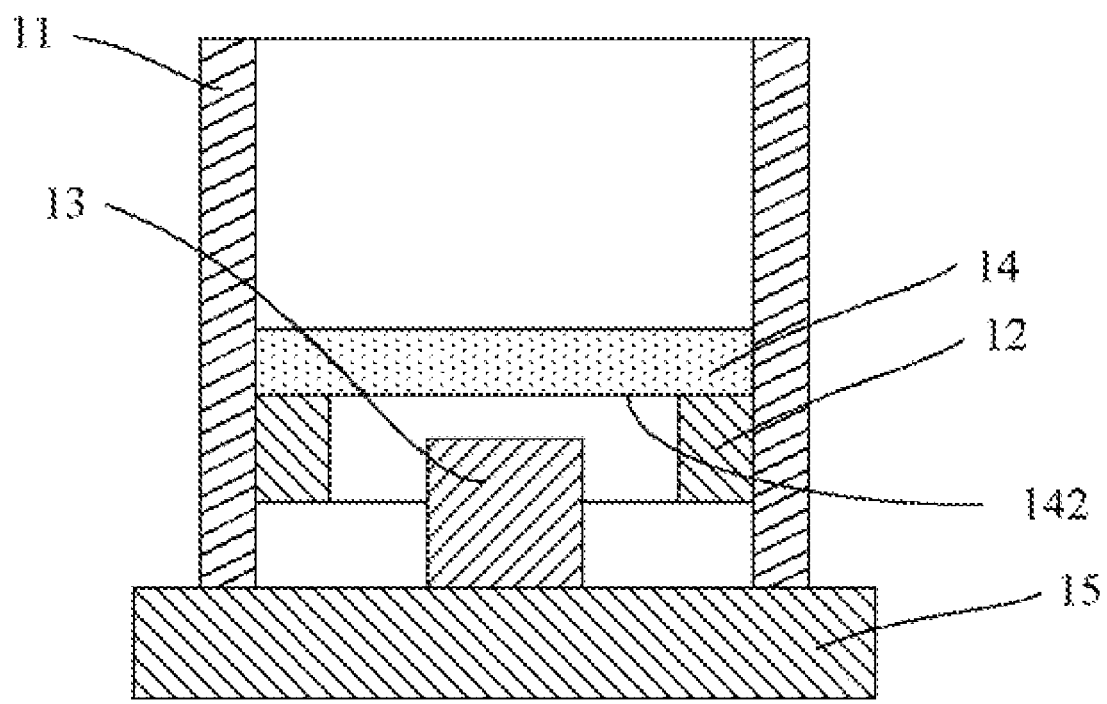

Referring to FIG. 3, the barrel 11 is attached to the base 15 in such a manner that the first magnet 13 faces a first surface 142 of the IR-cut filter 14 within the barrel 11. The barrel 11 can be attached to the base 15 using glue. Accordingly, adhesion strength between the barrel 11 and the base 15 should be greater than that between the IR-cut filter 14 and the spacer 12. The first magnet 13 can be a permanent magnet.

Figure 4:
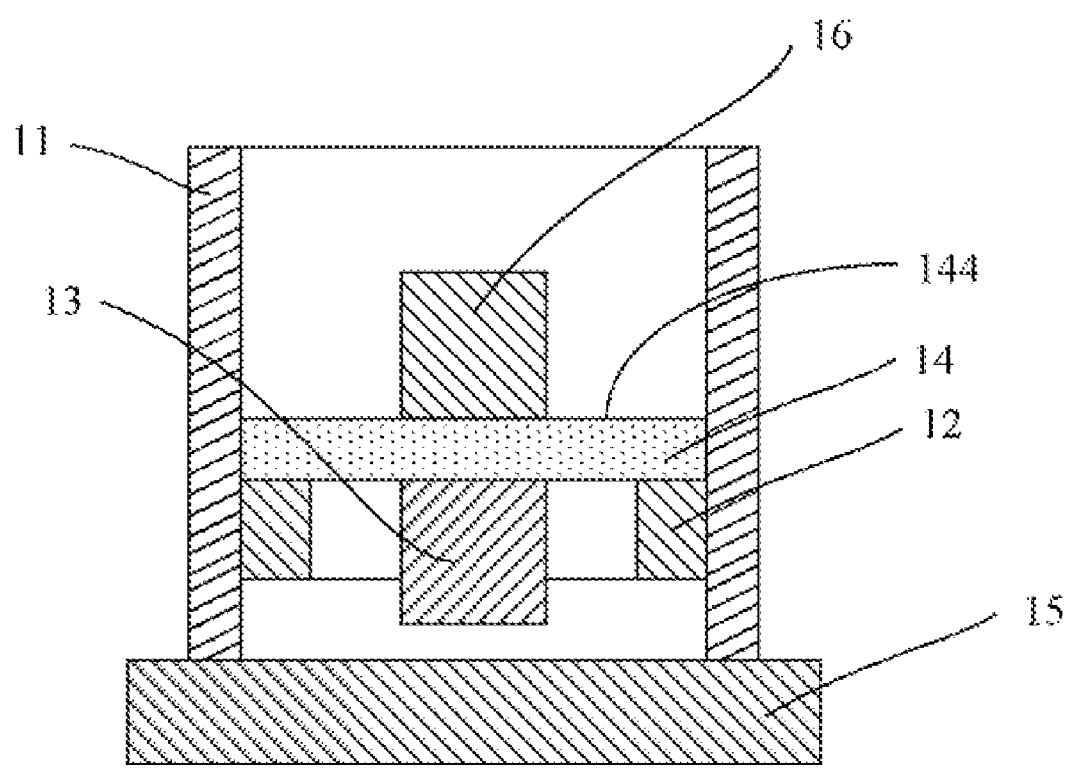

Referring to FIG. 4, a second magnet 16 is placed on a second surface 144 of the IR-cut filter 14 in such a manner that the second magnet 16 attracts the first magnet 13. In other words, when the first magnet 13 has a north pole close to the IR-cut filter 14, the second magnet 16 should have a south pole close to the IR-cut filter; when the first magnet 13 has a south pole close to the IR-cut filter 14, the second magnet 16 should have a north pole close to the IR-cut filter. Accordingly, the second magnet 16 attracts the first magnet due to an attractive force between them. The attractive force should be greater than the adhesion strength between the IR-cut filter 14 and the spacer 12. The second magnet 16 can be a permanent magnet.

Figure 5:
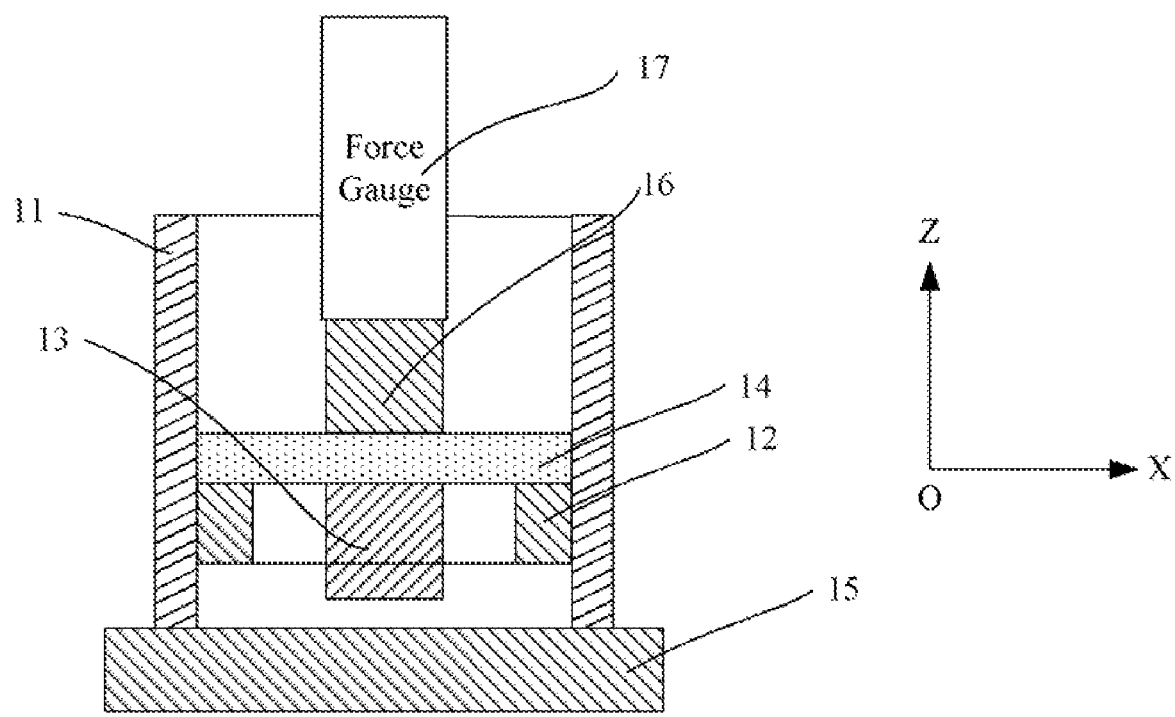

Referring to FIG. 5, a force gauge 17 is provided and attached to one end of the second magnet 16. The force gauge 17 can be selected from the group consisting of a mechanical force gauge and a digital force gauge.

Figure 6:
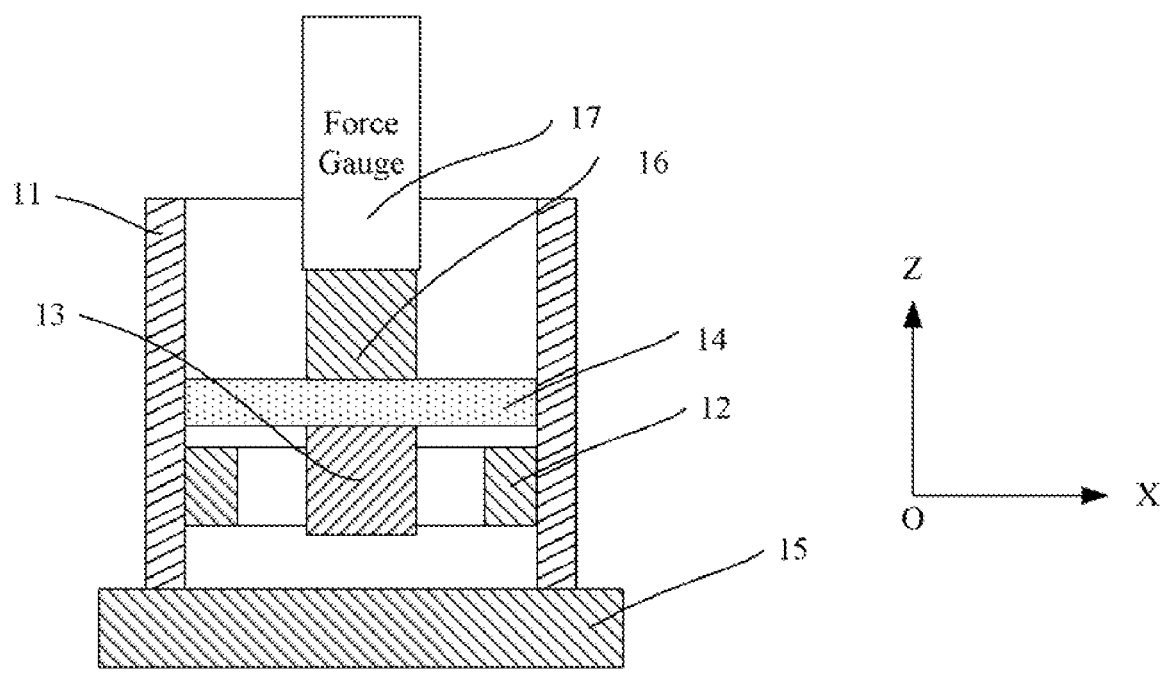

Referring to FIG. 6, an increasing force perpendicular to a plane of the optical element 14 is upwardly exerted on the force gauge 17. In other words, the force is exerted upwardly in a vertical direction (i.e., a Z axis) perpendicular to a horizontal direction (i.e., an X axis). When the force is less than the adhesion strength between the IR-cut filter 14 and the spacer 12, the IR-cut filter 14 stays on the spacer 12. The force is increased until the IR-cut filter 14 is pulled off from the spacer 12. A measurement result (Symbol F) of the force gauge 17 is obtained when the IR-cut filter 14 is pulled off the spacer 12.

Finally, the adhesion strength between the first and second optical elements is calculated based on the measurement result of the force gauge, and then the adhesion strength is displayed to a user.

When weight of the first magnet 13 and the second magnet 16 are very small compared to the adhesion strength between the IR-cut filter 14 and the spacer 12, they can be neglected. Therefore, the measurement result (F) of the force gauge 17 is equal to the adhesion strength between the IR-cut filter 14 and the spacer 12. Accordingly, the adhesion strength is calculated according to the following equation:

Adhesion Strength=$F$.

In order to calculate the adhesion strength more accurately, the weight (Symbol W1) of the first magnet 13 and the weight (Symbol W2) the second magnet 16 can be measured. Then the adhesion strength can be calculated according to the following equation:

Adhesion Strength=$F-W1-W2$.

When the force is not along the Z axis (For example, an angle between the force direction and the Z axis is a, wherein a is larger than zero degrees and less than 90 degrees), then the adhesion strength can be calculated according to the following equation:

Adhesion Strength=$F \sin a - W1 - W2$.

The above-mentioned method can measure the adhesion strength between the IR-cut filter 14 and the spacer 12 very easily. To measure the adhesion strength more accurately, a plurality of the adhesion strengths are measured, and then an average of the adhesion strengths is obtained.

Figure 7:
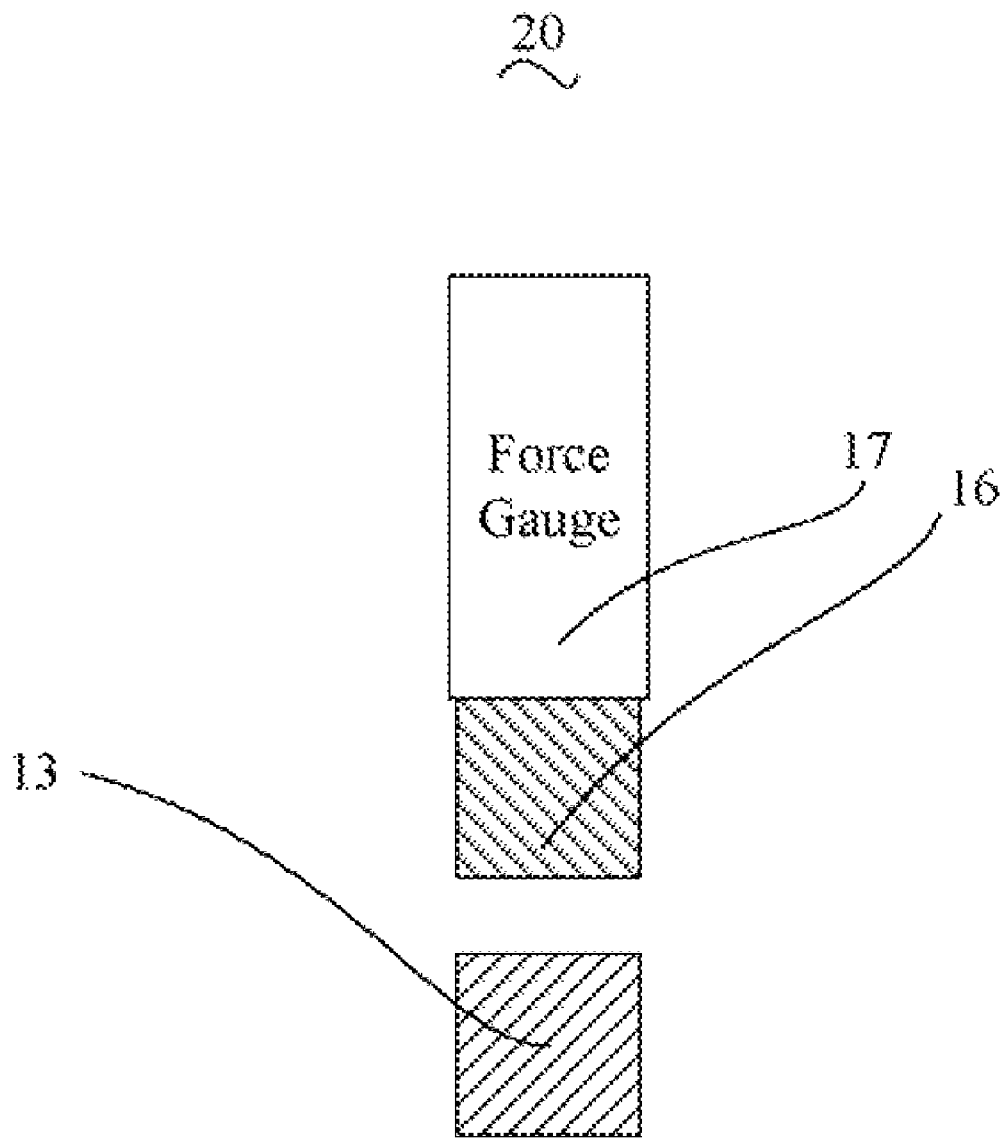
FIG. 7 is a schematic, cross-sectional view of a device for measuring the adhesion strength between the optical element and the spacer according to a preferred embodiment.

Referring to FIG. 7, a device 20 for measuring adhesion strength between a spacer and an optical element is also provided. The device 20 includes the force gauge 17, the first magnet 13, and the second magnet 16. The force gauge 17 is fixed to the second magnet 16. The first magnet 13 and the second magnet 16 are configured for magnetically attachment to opposite sides of the first optical element. An attractive force between the first magnet 13 and the second magnet 16 is greater than the adhesion strength between the spacer and the optical element.

While certain embodiments have been described and exemplified above, various other embodiments will be apparent to those skilled in the art from the foregoing disclosure. The present invention is not limited to the particular embodiments described and exemplified but is capable of considerable variation and modification without departure from the scope of the appended claims.

What is claimed is:

1. A method for measuring adhesion strength between a first optical element and a second optical element, the first optical element having a first surface and an opposite second surface, the second optical element being adhered to the first surface of first optical element, the second optical element defining an opening therein, whereby a portion of the first surface of the first optical element is exposed to an exterior, the method comprising the steps of:

placing a first magnet on the exposed portion of the first surface of the first optical element and a second magnet on the second surface of the first optical element in such a manner that the first magnet and the second magnet are magnetically attached onto the first and second surfaces of the first optical element, wherein a magnetic force between the first magnet and the second magnet is greater than the adhesion strength between the first optical element and the second optical element;

attaching the second magnet to a force gauge;

attaching the second optical element to a fixture;

exerting an increasing force onto the force gauge in a direction away from the second optical element until the first optical element is pulled off from the second optical element; and obtaining a measurement result of the force gauge, and then calculating the adhesion strength between the first and second optical elements based on the measurement result of the force gauge; and displaying the adhesion strength to a user.

2. The method as claimed in claim 1, wherein the force gauge can be selected from a group consisting of a mechanical force gauge and a digital force gauge.

3. The method as claimed in claim 1, wherein the first optical element is an infrared-cut filter.

4. The method as claimed in claim 3, wherein the spacer is fixed in a barrel which is secured to a base.

5. The method as claimed in claim 1, wherein the second optical element is a spacer.

6. The method as claimed in claim 1, wherein the first magnet is a permanent magnet.

7. The method as claimed in claim 1, wherein the second magnet is a permanent magnet.

8. The method as claimed in claim 1, wherein the adhesion strength is calculated according to the following equation:

Adhesion Strength=$F$, wherein F represents the measurement result of the force gauge.

9. The method as claimed in claim 1, wherein the adhesion strength is calculated according to the following equation:

Adhesion Strength=$F-W1-W2$, wherein F represents the measurement result of the force gauge, W1 represents a weight of the first magnet, W2 represents a weight of the second magnet.

10. A device for measuring adhesion strength between a first optical element and a second optical element, comprising:
   a force gauge;
   a first magnet;
   a second magnet, the second magnet being fixed to the force gauge; and
   the first optical element and the second optical element being bonded together using an adhesive;
   wherein the first magnet and the second magnet are configured for magnetically attaching to opposite sides of the first optical element, the force gauge is configured to measure the adhesion strength of the adhesive between the first optical element and the second optical element, and an attractive force between the first magnet and the second magnet is greater than the adhesion strength between the first optical element and the second optical element.

11. The device as claimed in claim 10, wherein the force gauge is selected from a group consisting of a mechanical force gauge and a digital force gauge.

12. The device as claimed in claim 10, wherein the first optical element is an infrared-cut filter.

13. The device as claimed in claim 10, wherein the first magnet is a permanent magnet.

14. The device as claimed in claim 10, wherein the second magnet is a permanent magnet.

15. The device as claimed in claim 10, wherein the second optical element is a spacer.

* * * * *